(12) United States Patent
Bichsel et al.

(10) Patent No.: US 7,238,174 B2
(45) Date of Patent: *Jul. 3, 2007

(54) VAGINAL CLEANING DEVICE

(76) Inventors: John Bichsel, 21 Sunset Bay Dr., Bellair, FL (US) 33756; Catherine Montgomery, 2400 1st St. #6, Indian Rocks Beach, FL (US) 33785

( * ) Notice: Subject to any disclaimer, the term of this patent is extended or adjusted under 35 U.S.C. 154(b) by 60 days.

This patent is subject to a terminal disclaimer.

(21) Appl. No.: 10/952,621

(22) Filed: Sep. 28, 2004

(65) Prior Publication Data
US 2006/0069338 A1    Mar. 30, 2006

(51) Int. Cl.
*A61F 13/15*    (2006.01)
*A61F 13/20*    (2006.01)

(52) U.S. Cl. .................. 604/385.17; 604/904
(58) Field of Classification Search ............... 604/330, 604/13, 17, 385, 14, 15, 181, 218, 385.17, 604/904
See application file for complete search history.

(56) References Cited

U.S. PATENT DOCUMENTS

| | | | |
|---|---|---|---|
| 3,063,452 A * | 11/1962 | Del Guercio | 604/378 |
| 3,724,463 A | 4/1973 | Vail | |
| 4,329,990 A * | 5/1982 | Sneider | 604/2 |
| 4,747,720 A * | 5/1988 | Bellehumeur et al. | 401/205 |
| 4,772,274 A | 9/1988 | Lukacs | |
| 5,045,058 A | 9/1991 | Demetrakopoulos | |
| 5,152,742 A * | 10/1992 | Simpson | 604/3 |
| 5,273,521 A * | 12/1993 | Peiler et al. | 604/13 |
| 5,397,312 A * | 3/1995 | Rademaker et al. | 604/218 |
| 5,401,240 A | 3/1995 | Yang | |
| 5,479,945 A * | 1/1996 | Simon | 128/885 |
| D379,508 S * | 5/1997 | Hudson et al. | D24/119 |
| 6,710,221 B1 * | 3/2004 | Pierce et al. | 604/361 |
| 2003/0014025 A1* | 1/2003 | Allen et al. | 604/361 |
| 2003/0120227 A1* | 6/2003 | Williams | 604/361 |
| 2004/0054345 A1* | 3/2004 | White | 604/385.17 |
| 2004/0087922 A1* | 5/2004 | Bobadilla | 604/361 |
| 2004/0172000 A1* | 9/2004 | Roe et al. | 604/361 |
| 2005/0177120 A1* | 8/2005 | Olson et al. | 604/361 |

* cited by examiner

*Primary Examiner*—Tatyana Zalukaeva
*Assistant Examiner*—Melanie J. Hand
(74) *Attorney, Agent, or Firm*—M. K. Silverman; Yi Li

(57) ABSTRACT

A vaginal cleaning device is disclosed, which includes an axial support post having a head disposed at the front end and a circular disk around the rear end, a tubular applicator body disposed around the post between the head and the disk, an applicator extension and a handle. Further disclosed is a vaginal cleaning device which includes a hollow axial support post having a head disposed at the front end, a circular disk around the rear end, a plurality of apertures around the body of the hollow axial support post, a tubular applicator body disposed around the post between the head and the disk, a hollow applicator extension and a fluid supply means connected to the applicator extension. A fluid can be delivered through the hollow applicator extension and the hollow axial support post into the tubular applicator body for cleaning the vagina.

20 Claims, 4 Drawing Sheets

VAGINAL CLEANING DEVICE

FIELD OF INVENTION

The present invention pertains to a personal vaginal cleaning and hygiene device.

BACKGROUND OF THE INVENTION

The vagina is a relatively long hollow, tube like structure that extends from the cervix at the outer end of the uterus down to the labia minora. The interior of the vagina is composed of a mucous membrane and an outer, smooth muscle closely attached to it. While glands are present in the vaginal lining itself, vaginal secretions can arise from the glands in the cervical canal of the uterus such as Bartholin's and Skene's glands. Normally such secretions are clean, but occasionally debris in the form of blood or deposition of seminal fluid can accumulate. Accordingly, it is desirable at times to be able to have a convenient disposable applicator to clean and refresh the vaginal canal to add to or treat the vaginal canal with medications, germicides, or deodorants.

U.S. Pat. No. 5,045,058 by Demetrakopoulos cleanses the vagina by providing an apparatus that delivers lather to the vaginal canal. Vaginal cleaning devices have been addressed in the prior art in terms of a swabbing applicator, as may be seen in U.S. Pat. No. 3,724,463 to Vail. Also, other vaginal cleaning devices that have been addressed in the prior art include a syringe apparatus as may be seen in U.S. Pat. No. 4,772,274 to Lukacs and U.S. Pat. No. 5,401,240 to Yang. However, these devices do not satisfactorily consider all issues of size, convenience, portability, simplicity of construction, and effectiveness that are addressed herein.

SUMMARY OF THE INVENTION

In one embodiment, the present invention is directed to a vaginal cleaning device. The vaginal cleaning device comprises an applicator comprising an axial support post, a head with a rear surface connected to the front end of the axial support post, and a circular disk disposed around the rear end of the axial support post; and a tubular applicator body having a central opening, disposed around the axial support post between the head and the circular disk; an applicator extension with the front end thereof integrally dependent from the rear end of the axial support post; and handle means connected to the rear end of the applicator extension. The tubular applicator body is made of a flexible absorbent material.

In a further embodiment, the vaginal cleaning device comprises an applicator comprising a hollow axial support post having a head with a rear surface connected to the front end of the axial support post, and a circular disk disposed around the rear end of the axial support post; the hollow axial support post having a plurality of apertures disposed around thereof; and a tubular applicator body having a central opening, disposed around the axial support post between the head and the circular disk; a hollow applicator extension having the front end thereof integrally dependent from the rear end of the hollow axial support post, with the hollow applicator extension in fluid communication with the hollow axial support post; and a fluid supply means attached to the rear end of the hollow applicator extension. A fluid supply means can be a squeezable liquid container for supplying a fluid to the tubular applicator body, and it also functions as a handle.

The plurality of apertures can be slots aligned along the longitudinal axis, or aligned with an angle to the longitudinal axis, of the hollow axial support post.

It is an object of the present invention to provide a vaginal cleaning device having functions of cleaning, deodorizing, and medicating the vaginal canal.

Another object is to provide a portable, efficient and effective means to cleanse the vaginal canal prior to or after sexual intercourse.

It is a yet further object to provide a vaginal cleaning device that is more effective than prior art solutions of lathering or scrubbing, and more convenient to use then syringe-like devices.

The above and yet other objects and advantages of the present invention become apparent from the hereinafter set forth Brief Description of the Drawings, Detailed Description of the Invention, and claims appended herewith.

BRIEF DESCRIPTION OF THE DRAWINGS

FIG. 5 is a top view of the vaginal cleaning device of FIG. 1, without the cap.

FIG. 6 is a top view of the device FIG. 5 without the tubular applicator body.

DETAILED DESCRIPTION OF THE INVENTION

Figure 1:
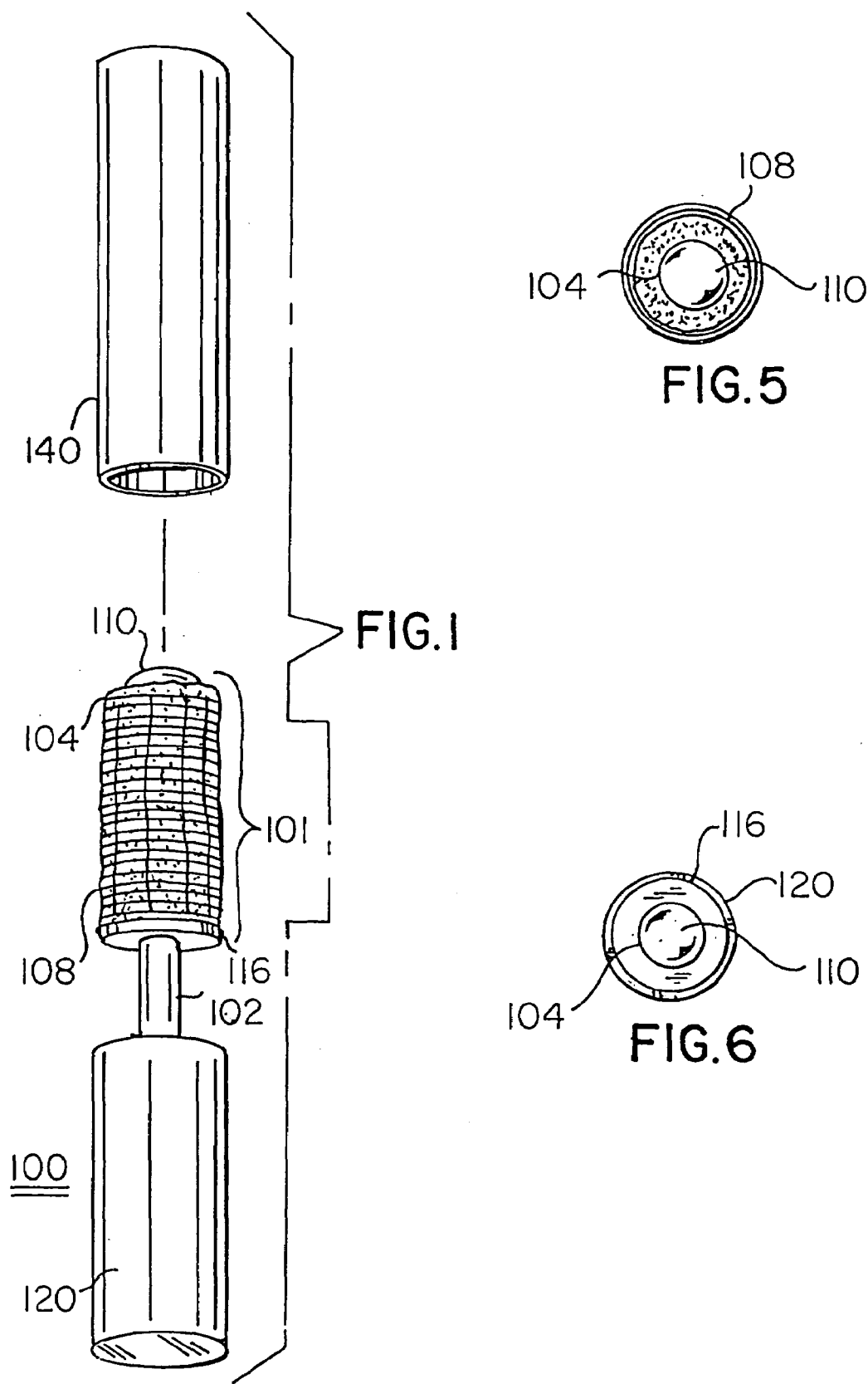
FIG. 1 is a perspective view of the first embodiment of the vaginal cleaning device of the present invention.
Figure 2:
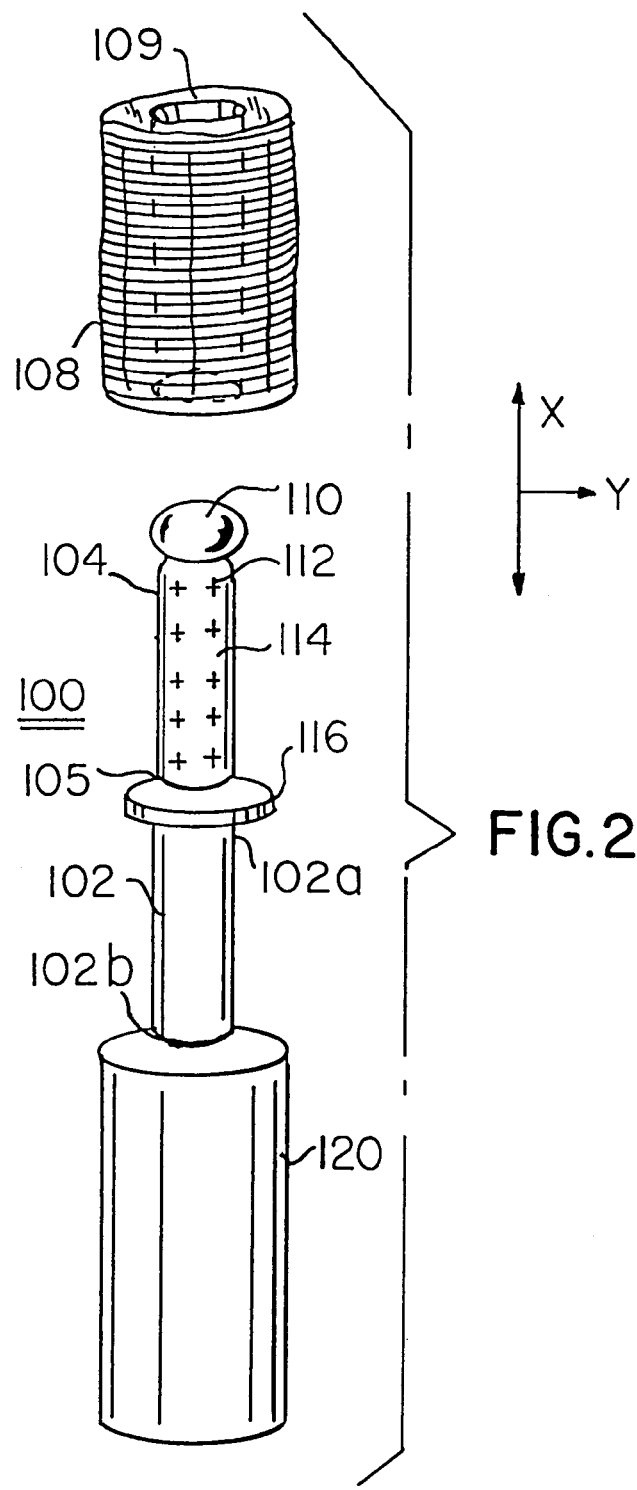
FIG. 2 is a perspective, exploded view of the vaginal cleaning device of FIG. 1.

In the first embodiment, the present invention provides a vaginal cleaning device, as shown in FIGS. 1 and 2. The vaginal cleaning device 100 comprises an applicator 101, an applicator extension 102 and a handle 120.

The applicator 101 comprises an axial support post 114 and a tubular applicator body 108. The axial support post 114 has a front end 104 and an opposing rear end 105; a head 110 with a rear surface connected to the front end 104; and a circular disk 116 disposed around the rear end 105. The applicator extension 102 has a front end 102a and a rear end 102b, with the front end 102a integrally dependent from the rear end 105 of the axial support post 114. The handle means 120 is connected to the rear end 102b of the applicator extension 102. Preferably, the handle means 120 is an integral part of the applicator extension 102.

The tubular applicator body 108 has a central opening 109, and is disposed around axial support post 114 between the head 110 and the circular disk 116. The tubular applicator body 108 is removable from the axial support post 114 by sliding over the head 110. It is made of a porous flexible absorbent material, such as a sponge material, and ribbed cotton as shown in FIG. 1. Preferably, an FDA approved material, such as a sponge material made of hydrophilic polyurethane foam, is used. The porous surface of the sponge helps gently scrubbing the interior of the vagina, and enhances the effectiveness of cleaning. The tubular applicator body 108 is disposable, which can be discarded after one time use. A new tubular applicator body 108 can be installed onto the axial support post 114 by simply sliding over the head 110 though the central opening 109 thereof.

The head 110 has a semi-spherical front surface for comfortable delivery of the applicator 101 into the vagina of a user. The rear surface of the head 110 is substantially planar. FIGS. 5 and 6 show top views of the applicator 101 with, and without the tubular applicator body 108. The head 110 has an outer diameter larger than the outer diameter of the axial support post 114 and the inner diameter of the opening 109 of the tubular applicator body 108, thereby retaining the tubular applicator body 108 behind the head 110. Preferably, the outer diameter of the axial support post 114 is in a range from about ⅜ to about ½ inch. The outer diameter of the head is preferably from about ⅜ to about ⅝ inches. Preferably, the lengths of the axial support post 114 and the tubular applicator body 108 are from about 2.0 to about 3.0 inches.

Figure 4:
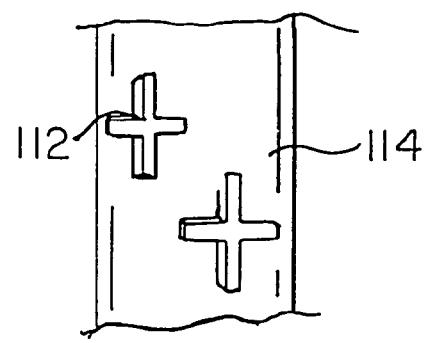
FIG. 4 is an enlarged view of the retention means of the axial support post of the device shown in FIG. 3.
Figure 3:
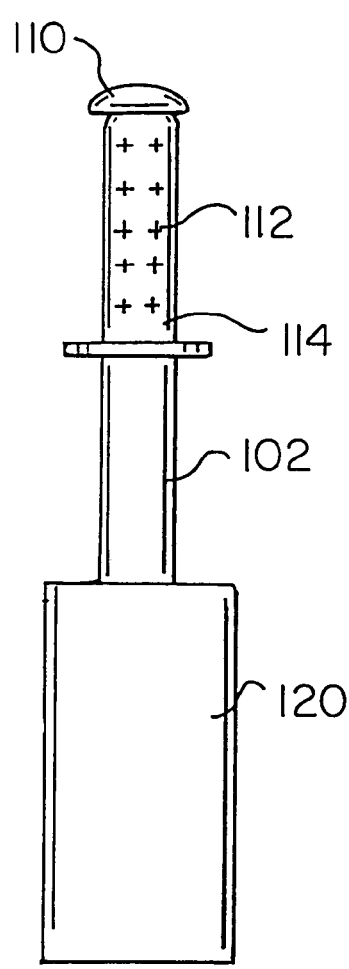
FIG. 3 is a side view of part of the vaginal cleaning device of FIG. 1.

Preferably, the axial support post 114 further comprises retention means 112. As shown in FIGS. 3 and 4, the retention means 112 are a plurality of protruding short rims arranged in a shape of a cross. However, it should be understood that other shapes and geometries can also be used for the retention means. The retention means 112 are disposed around the surface of the axial support post 114, which assists to hold the tubular applicator body 108 in place during use. The combination of the head 110, the circular disk 116 and the retention means 112 maintains the position of the tubular applicator body 108 and prevents dislocation of the tubular applicator body 108 during use. Optionally, the front end 104 of the axial support post 114 can be tapered in the direction toward the head 110, as shown in FIGS. 2 and 3.

The axial support post, head and retention means can be made of a low density polyethylene, preferably, FDA approved material such as USP Class 6B1-ISO10993. Moreover, the axial support post, head, and retention means can also be made of other FDA approved moldable plastic materials.

The vaginal cleaning device 100 can further comprise an applicator cap 140. In one embodiment, the applicator cap 140 is proportioned for press- or snap-fittable enclosure of the tubular applicator body 108.

When in use, the user removes the applicator cap 140, inserts the applicator 101 into the vagina, then turns or moves the applicator 101 forward and backward to clean the vagina. Furthermore, the user can also wet the tubular applicator body with a fluid supply source, such as tap water, and then use the vagina cleaning device 100 as described above.

Figure 7:
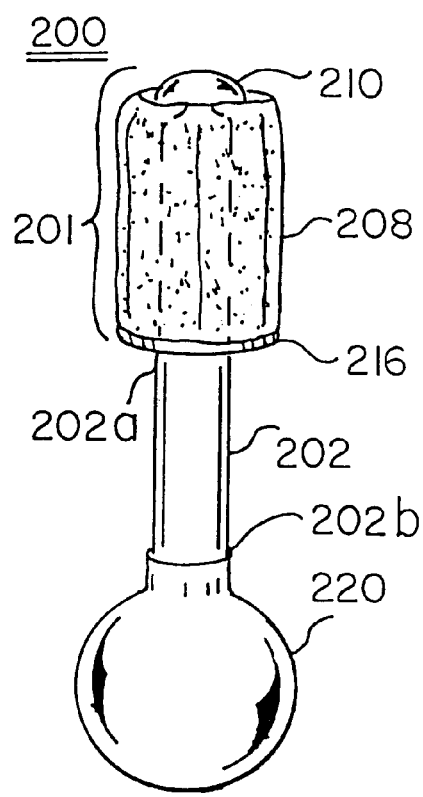
FIG. 7 is a perspective view of the vaginal cleaning device of a second embodiment of the present invention.
Figure 8:
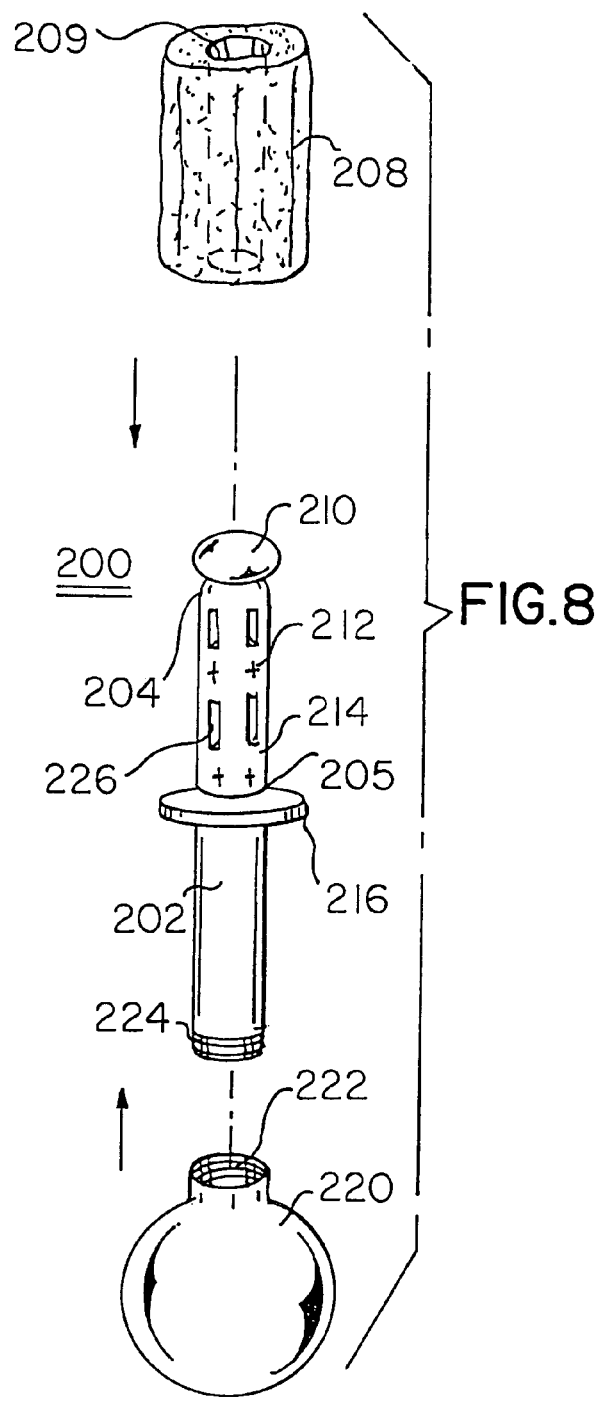
FIG. 8 is a perspective, exploded view of the vaginal cleaning device of FIG. 7.

In a second embodiment, the present invention provides a vaginal cleaning device 200 as shown in FIGS. 7 and 8. The vaginal cleaning device 200 comprises an applicator 201, a hollow applicator extension 202 and a fluid supply means 220.

The applicator 201 comprises a hollow axial support post 214 and a tubular applicator body 208. The hollow axial support post 214 has a front end 204 and an opposing rear end 205; a head 210 with a rear surface connected to the front end 204; and a circular disk 216 disposed around the rear end 205. The hollow axial support post 214 has a plurality of apertures 226 disposed around the body of the hollow axial support post 214, for dispensing a fluid. As shown in FIG. 8, the apertures 226 are slots aligned along the longitudinal axis of the hollow axial support post 214. It should be understood that the apertures 226 can also have other shapes and arrangement.

The hollow applicator extension 202 has a front end 202a and a rear end 202b, with the front end 202a integrally dependent from the rear end 205 of the hollow axial support post 214. The hollow applicator extension 202 is in fluid communication with the hollow axial support post 214.

The tubular applicator body 208 has a central opening 209, and is disposed around the hollow axial support post 214 between the head 210 and the circular disk 216. The structure, material and property of the tubular applicator body 208 are the same as those of tubular applicator body 108 described previously.

Similarly, the structure, material and function of the head 210, circular disk 216 and retention means 212 are the same as those described previously in the first embodiment, for the head 110, circular disk 116 and retention means 112.

The fluid supply means 220 can be a liquid container, such as a squeezable bottle, or a squeezable bag as shown in FIG. 8. The fluid supply means 220 is connected to the rear end 202b of the hollow applicator extension 202 by a connection means. In the embodiment shown in FIG. 8, the squeezable bag is connected to the hollow applicator extension 202 by a thread connection. As shown, the rear end 202b of the hollow applicator extension 202 has external threads 224, and the squeezable bag has complementary internal threads for mutual connection. It should be understood that other suitable connection means with a fluid-tight seal can also be used for connecting the fluid supply means 220 to the hollow applicator extension 202. In use, the fluid supply means 220 also functions as a handle for holding the vagina cleaning device 200.

When in use, the user inserts the applicator 201 into the vagina, then squeezes the fluid supply means 220 to force the fluid contained inside to the hollow axial support post 214 through the applicator extension 202. The fluid is dispensed through the apertures 226 into the tubular applicator body 208. Then the user can turn or move the applicator 201 forward and backward to clean the vagina.

Figure 9:
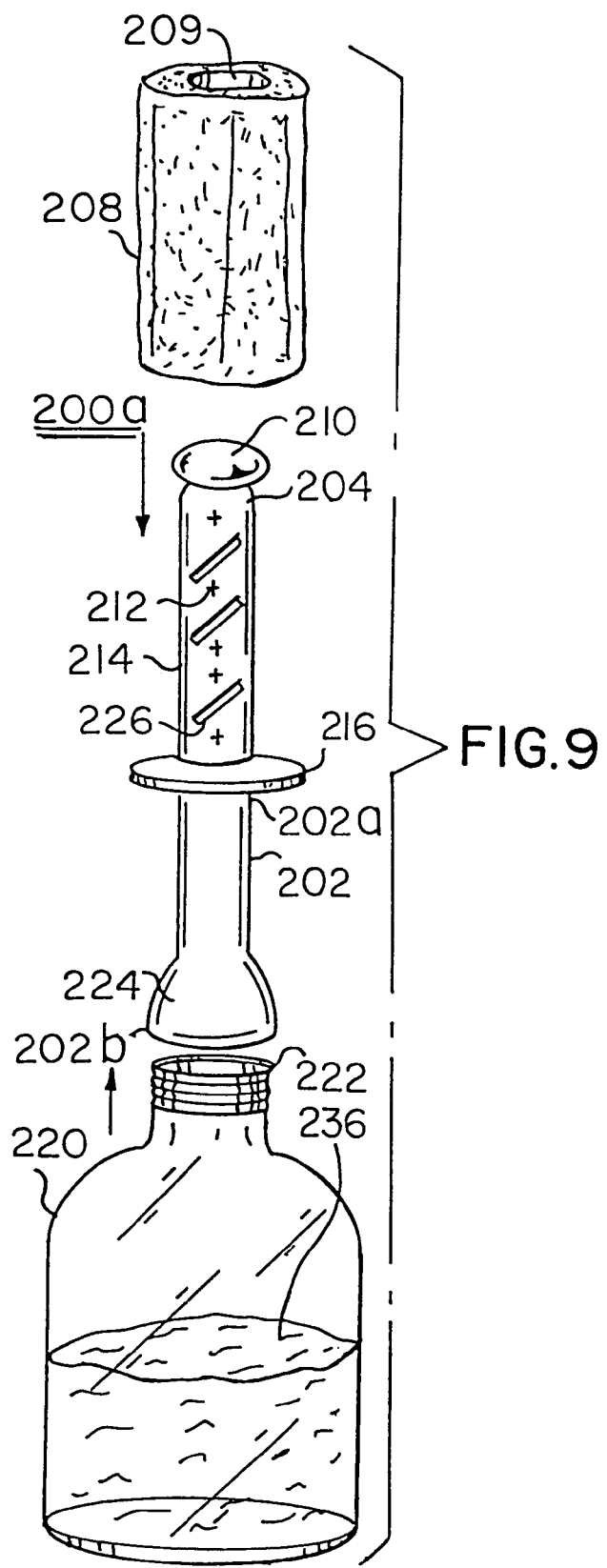
FIG. 9 is a perspective, exploded view of a variation of the second embodiment shown in FIGS. 7 and 8, defining a variation of the second embodiment of the present invention.

FIG. 9 shows a variation of the vaginal cleaning device 200. As shown, apertures 226 are slots aligned with an angle to the longitudinal axis of the hollow axial support post 214. In this embodiment, the rear end 202b of the hollow applicator extension 202 has an enlarged interface portion for engaging with the liquid bottle 220. The fluid contained in the fluid supply means 220, such as that shown in FIG. 9 as fluid 236, can be water, or a pharmaceutically acceptable cleaning agent, or deodorant. Optionally, the fluid can also contain one or more medicines for treatment use.

While there has been shown and described the preferred embodiment of the instant invention it is to be appreciated that the invention may be embodied otherwise than is herein specifically shown and described and that, within said embodiment, certain changes may be made in the form without departing from the underlying ideas or principles of this invention as set forth in the claims appended herewith.

We claim:

1. A vaginal cleaning device comprising:
   (a) an applicator comprising:
   (i) an axial support post having a front end and an opposing rear end, a head having an outer diameter larger than an outer diameter of said axial support post, connected to said front end of said axial support post; and a circular disk disposed around said rear end of said axial support post; and (ii) a tubular applicator body having a central opening, disposed around said axial support post and retained between a rear surface of said head and said circular disk; wherein said tubular applicator body is made of a flexible absorbent material;

(b) an applicator extension having a front end and a rear end, with said front end thereof integrally dependent from said rear end of said axial support post; and (c) handle means connected to said rear end of said applicator extension.

2. The vaginal cleaning device as recited in claim 1 further comprising an applicator cap.

3. The vaginal cleaning device as recited in claim 1, wherein said axial support post has retention means on an external surface thereof, for retaining said tubular applicator body in position.

4. The vaginal cleaning device as recited in claim 3, wherein said retention means is a plurality of protruding rims positioned around said axial support post.

5. The vaginal cleaning device as recited in claim 1, wherein said head has a semi-spherical front surface, and said rear surface thereof is substantially planar.

6. The vaginal cleaning device as recited in claim 1, wherein said front end of said axial support post tapers in a direction toward said head.

7. The vaginal cleaning device as recited in claim 1, wherein said tubular applicator body is removable from said axial support post over said head.

8. The vaginal cleaning device as recited in claim 1, wherein said flexible absorbent material is a sponge material made of hydrophilic polyurethane foam.

9. The vaginal cleaning device as recited in claim 1, wherein said flexible absorbent material is ribbed cotton.

10. A vaginal cleaning device comprising:

(a) an applicator comprising:

(i) a hollow axial support post having a front end and an opposing rear end, a head having an outer diameter larger than an outer diameter of said axial support post, connected to said front end of said axial support post; and a circular disk disposed around said rear end of said axial support post; said hollow axial support past having a plurality of apertures disposed around thereof; and (ii) a tubular applicator body having a central opening, disposed around said axial support post and retained between a rear surface of said head and said circular disk; wherein said tubular applicator body is made of a flexible absorbent material;

(b) a hollow applicator extension having a front end and a rear end, with said front end thereof integrally dependent from said rear end of said hollow axial support post; wherein said hollow applicator extension is in fluid communication with said hollow axial support post; and (c) a fluid supply means attached to said rear end of said hollow applicator extension.

11. The vaginal cleaning device as recited in claim 10, wherein said plurality of apertures are slots aligned along a longitudinal axis of said hollow axial support post.

12. The vaginal cleaning device as recited in claim 10, wherein said plurality of apertures are slots aligned with an angle to a longitudinal axis of said hollow axial support post.

13. The vaginal cleaning device as recited in claim 10, wherein said fluid supply means is a liquid container containing a cleaning fluid.

14. The vaginal cleaning device as recited in claim 10, wherein said axial support post has retention means on an external surface thereof, for retaining said tubular applicator body in position.

15. The vaginal cleaning device as recited in claim 14, wherein said retention means is a plurality of protruding rims positioned around said axial support post.

16. The vaginal cleaning device as recited in claim 10, wherein said head has a semi-spherical front surface, and said rear surface thereof is substantially planar.

17. The vaginal cleaning device as recited in claim 10, wherein said front end of said axial support post tapers in a direction toward said head.

18. The vaginal cleaning device as recited in claim 10, wherein said tubular applicator body is removable from said axial support post over said head.

19. The vaginal cleaning device as recited in claim 10, wherein said flexible absorbent material is sponge material made of hydrophilic polyurethane foam.

20. The vaginal cleaning device as recited in claim 10, wherein said flexible absorbent material is ribbed cotton.

* * * * *